(12) United States Patent
Larson et al.

(10) Patent No.: US 8,076,151 B2
(45) Date of Patent: Dec. 13, 2011

(54) ULTRA-SENSITIVE TEMPERATURE SENSING AND CALORIMETRY

(75) Inventors: Dale N. Larson, Waban, MA (US); Gregory Kowalski, Beverly, MA (US)

(73) Assignees: President and Fellows of Harvard College, Cambridge, MA (US); Northeastern University, Boston, MA (US)

( * ) Notice: Subject to any disclaimer, the term of this patent is extended or adjusted under 35 U.S.C. 154(b) by 0 days.

(21) Appl. No.: 12/448,836

(22) PCT Filed: Jan. 16, 2008

(86) PCT No.: PCT/US2008/000580
§ 371 (c)(1),
(2), (4) Date: Jan. 12, 2010

(87) PCT Pub. No.: WO2008/088829
PCT Pub. Date: Jul. 24, 2008

(65) Prior Publication Data
US 2010/0120163 A1    May 13, 2010

Related U.S. Application Data

(60) Provisional application No. 60/885,025, filed on Jan. 16, 2007.

(51) Int. Cl.
*G01N 25/20* (2006.01)
*G01N 25/00* (2006.01)
(52) U.S. Cl. .............................. 436/147; 422/51; 422/50
(58) Field of Classification Search .................. 436/147; 422/51, 50
See application file for complete search history.

(56) References Cited

U.S. PATENT DOCUMENTS

| 2003/0036204 A1 | 2/2003 | Stark |
| 2005/0260653 A1 | 11/2005 | Labaer |
| 2006/0159585 A1* | 7/2006 | Torres et al. .................... 422/51 |

FOREIGN PATENT DOCUMENTS

EP    1686360 A1    8/2006

OTHER PUBLICATIONS

Herminghaus et al., "Surface Plasmon Enhanced Transient Thermoreflectance," *Appl. Phys.* A 51:350-353 (1990).
International Written Opinion for PCT/US2008/000580 mailed Jul. 30, 2009.
International Search Report for PCT/US2008/000580 mailed Sep. 26, 2008.

* cited by examiner

*Primary Examiner* — Christine T Mui
(74) *Attorney, Agent, or Firm* — Wolf, Greenfield & Sacks, P.C.

(57) ABSTRACT

Methods and apparatus for ultra-sensitive temperature sensing and calorimetry. Radiation is directed at a thin electrically conductive film having one or more small apertures. The incident radiation excites surface plasmons on a first surface of the electrically conductive film, and energy associated with the surface plasmons couples to an opposite surface of the electrically conductive film, where surface plasmon-enhanced radiation (SPER) is emitted from the aperture(s). A temperature-sensitive fluid or solid dielectric material is disposed contiguous with at least a portion of the electrically conductive film, such that a temperature change in the dielectric material alters a resonance condition for the SPER. Measurable changes in the SPER due to altered resonance conditions provide for an ultrasensitive temperature sensor that can detect small temperature changes in the dielectric material. The disclosed methods and apparatus may be used for a variety of applications including, but not limited to, nanoscale to microscale calorimetry for pharmaceutical and biotechnology products, combustion sensing, explosive detection, and biotoxin monitoring.

30 Claims, 11 Drawing Sheets

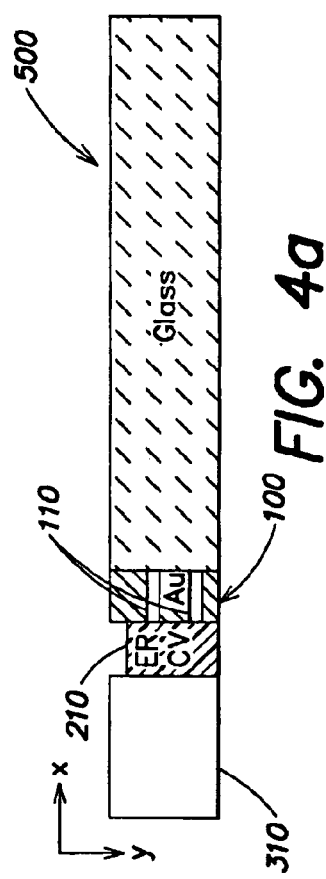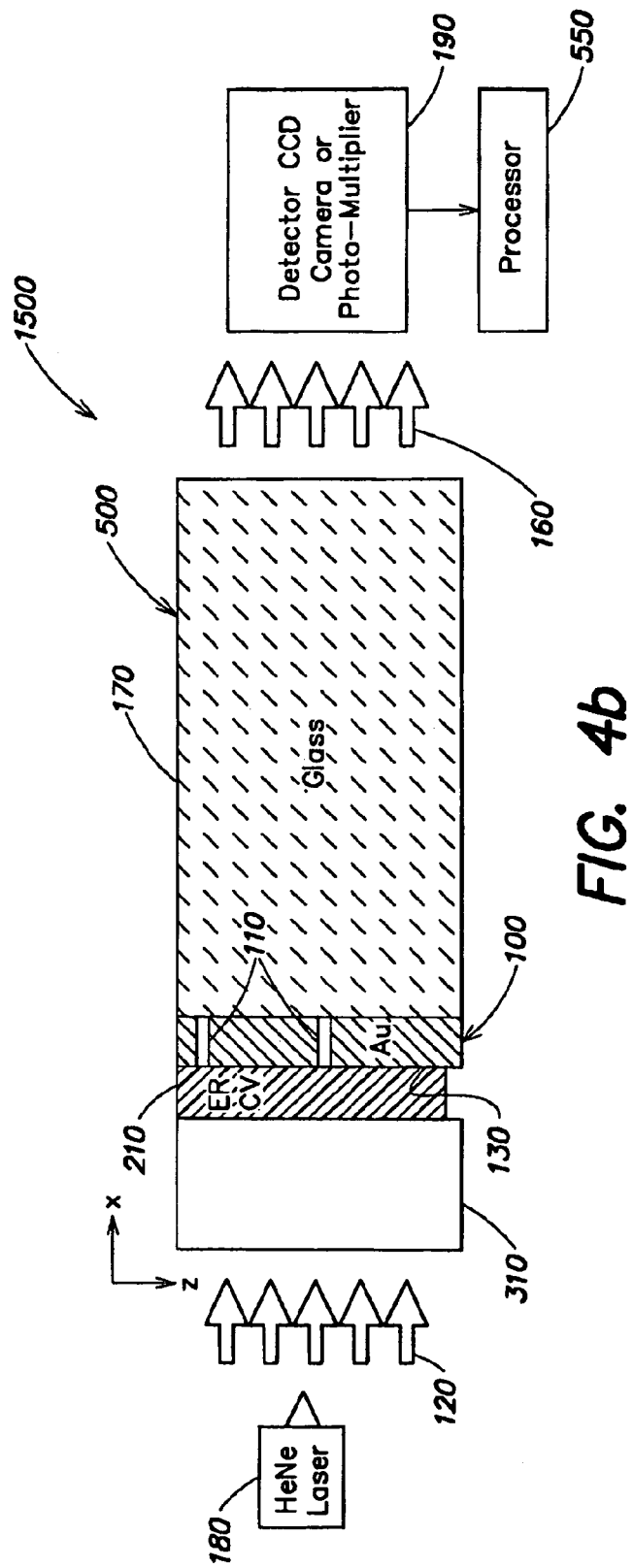

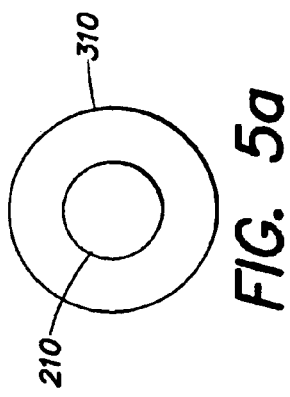
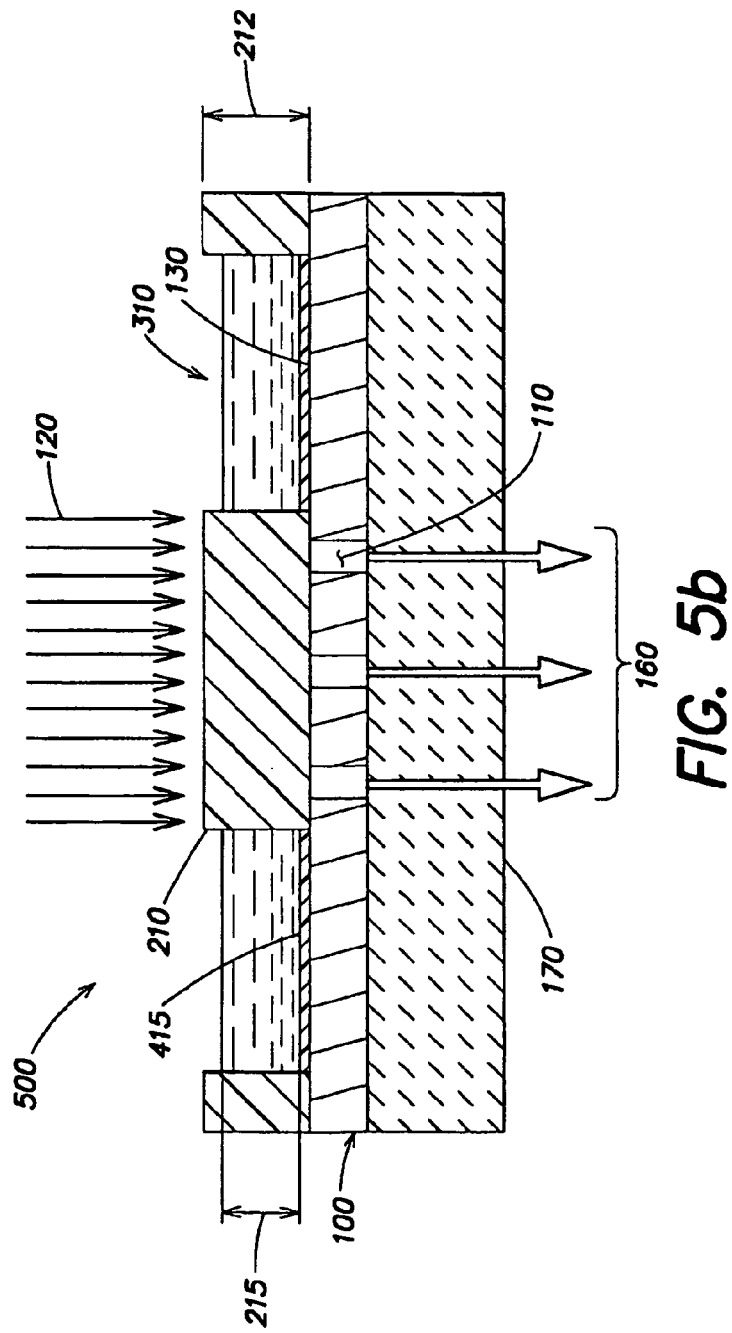
FIG. 5a
FIG. 5b

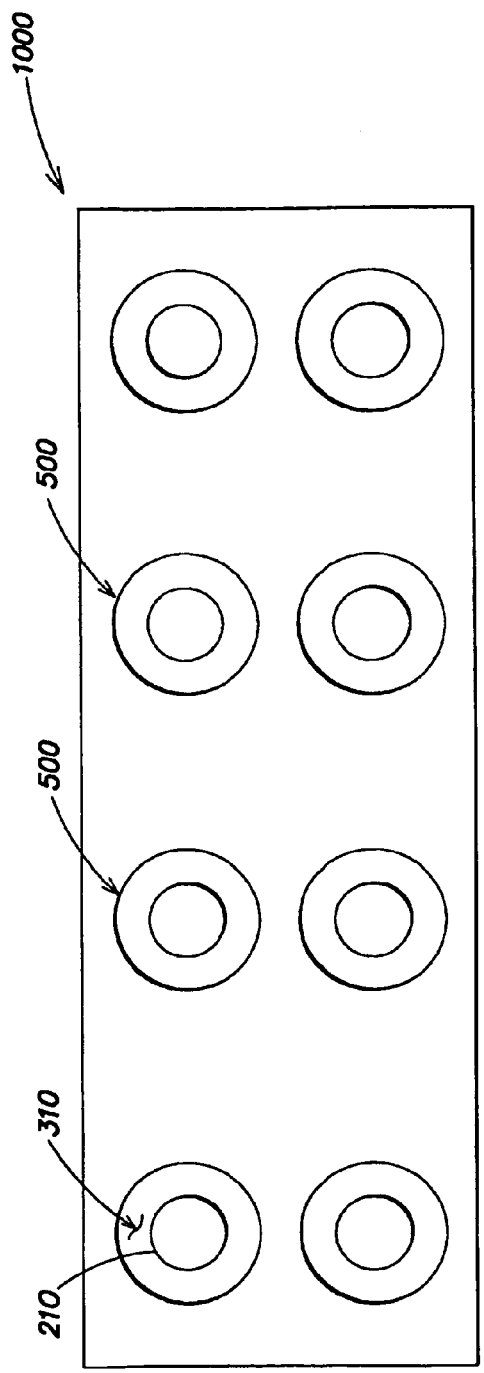
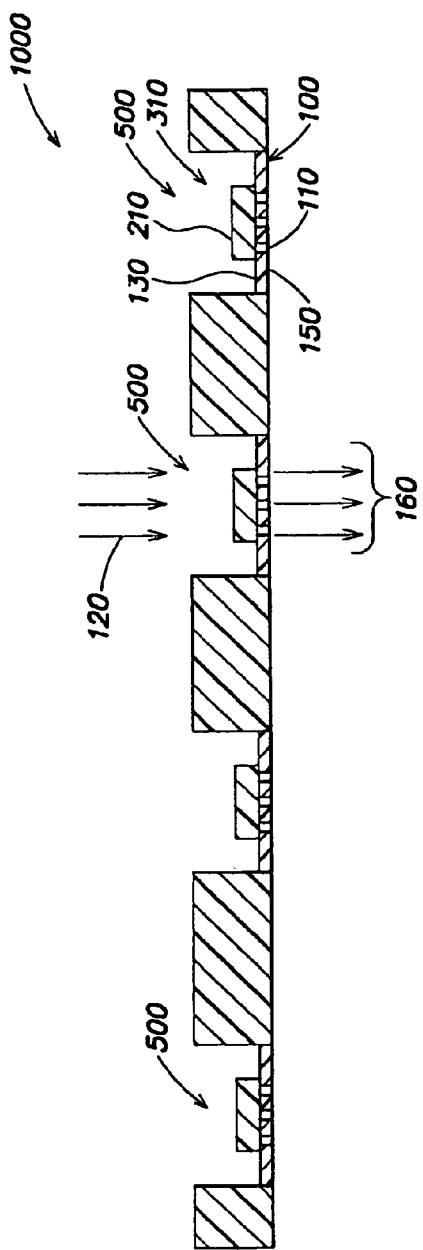
FIG. 11a
FIG. 11b

ULTRA-SENSITIVE TEMPERATURE SENSING AND CALORIMETRY

Related Applications

The present application is a 371 national stage application of PCT/US2008/000580, which claims the benefit under 35 U.S.C. §119(e) of U.S. provisional patent application Ser. No. 60/885,025 filed Jan. 16, 2007.

FIELD OF THE INVENTION

The present invention relates generally to temperature sensing, and more specifically to sensing temperature changes associated with chemical reactions via surface plasmon-enhanced radiation.

BACKGROUND

Detecting and characterizing the thermodynamics of a chemical reaction provides insight into the mechanism by which the chemical reaction occurs. For example, the detection and characterization of binding interactions (e.g., protein-protein interactions, proteins-DNA, drug-protein interactions) are central to basic biological research and pharmaceutical research and development (R&D). Many analytical techniques have been developed to study various types and aspects of binding interactions. Some examples of these techniques include Enzyme-Linked ImmunoSorbent Assay (ELISA), mass spectrometry, fluorescence resonance energy transfer, fluorescence correlation spectroscopy, fluorescence anisotropy, protein arrays, nucleic acid microarrays, and calorimetry. Calorimetry is a particularly advantageous method used to study the thermodynamics of binding interactions. Calorimetry measures the energy released or absorbed by a reaction over a range of reactant concentrations, and uses this information to determine the thermodynamic properties, stoichiometry, and equilibrium binding constant for the reaction.

In a typical calorimetry experiment, the heat of reaction, enthalpy ($\Delta H$), is measured and from this measurement the Gibbs free energy, entropy, affinity constant, and stoichiometry are determined. A reaction in which heat is released is exothermic (positive $\Delta H$), whereas a reaction that absorbs heat is endothermic (negative $\Delta H$). An accurate measurement of enthalpy and subsequent determination of entropy allows for an assessment of the relative contributions of each to the binding interactions of particular compounds. Understanding these relative contributions allows for the selection of compounds that are more readily optimized for various applications (e.g., pharmaceutical development).

FIG. 1 generally outlines a calorimetry process and exemplary information obtained from the process. In FIG. 1, a reaction of interest 50 comprises a drug candidate 52 and a target protein 54. By measuring the heat 56 released or absorbed by the reaction, information 58 may be derived from the heat signature of the reaction 50, and the information 58 may be used, for example, to help determine the potential efficacy of the drug candidate. The information 58 may include indicators of bioactivity, such as the number of bonds formed, type of bonds, physical fit of the ligand (drug candidate) in the binding site of the target protein, binding kinetics, and stoichiometry, although other information may also be included in information 58.

Enthalpy ($\Delta H$) is driven primarily by the number and type of bonds in the binding reaction, and provides an indication of specific interactions between binding partners. Enthalpy determinations help ensure specificity, selectivity and adaptability of the binding compounds. More specifically, enthalpy corresponds to the energy associated with the net change in noncovalent bonds between binding partners. Noncovalent bonds help maintain the three-dimensional structure of large molecules such as proteins and nucleic acids, and are involved in many biological processes in which large molecules bind specifically but transiently to one another. As such, a larger $\Delta H$ suggests a better complementarity of bonds in the interface, and a comparison of $\Delta H$'s of binding reactions provides useful information for selecting between compounds having similar affinities, thereby determining which compounds should undergo further chemical modification. By comparison, entropy is driven primarily by the geometry of the binding compounds, and may play a lesser role in characterizing binding specificity.

Temperature sensors conventionally employed for determining the heat of a chemical reaction in calorimetry studies include thermocouples, thermopiles, and/or thermistors. For example, in one calorimetry study described by Torres et al. (Torres et al. Enthalpy Arrays, PNAS 101, 9517-9522, 2004), enthalpy arrays are based on amorphous silicon thermistors fabricated via photolithography with 50 micrometer design rules, where each sensor includes of two thermistors connected in a Wheatstone bridge configuration. In Torres' system, samples consisting of two small drops of liquid, one for each reactant, are electrostatically merged, and the difference between the temperatures of the respective sensors indicates the heat of the reaction.

Other temperature sensing methods have used changes in optical properties to infer temperature changes in reactions with immobilized reactants (e.g., Zhang et al., Calorimetric biosensors with integrated microfluidic channels. Biosensors and Bioelectronics, 19, 1733-1743, 2004). However, these optical-based temperature-sensing approaches often lack a desired sensitivity for detecting small changes in temperature that typically characterize chemical reactions with small enthalpy changes.

SUMMARY

Applicants have recognized and appreciated that conventional methods and apparatus for sensing temperature changes associated with chemical reactions are not adequate for many applications. For example, Applicants have recognized that some conventional temperature-based methods (e.g., calorimetry) for assessing the binding interactions of biological and/or pharmaceutical compounds, and apparatus for implementing such methods, have not gained widespread use due to several limitations including, but not limited to, inadequate sensitivity for low enthalpy ($\Delta H$) reactions, the relatively large amount of reactants required, and the low sample throughput using such methods. Contributing factors to low throughput include long experiment run times (60 to 90 minutes) and the need to sequentially run controls to assess the significance of confounding effects. In particular, for applications such as pharmaceutical development, temperature-based evaluation methods such as calorimetry are typically only used at a point in the pharmaceutical R&D developmental process when the number of compounds being pursued has been selectively narrowed using other methods that require smaller masses of the reactants.

In view of the foregoing, embodiments of the present invention mitigate at least some of the aforementioned limitations associated with conventional temperature sensing techniques typically employed in calorimetry studies, and describe methods and apparatus for ultra-sensitive temperature sensing using surface plasmon-enhanced radiation.

One embodiment of the present invention is directed to a calorimetry method. The calorimetry method comprises measuring an enthalpy associated with at least one chemical reaction based at least in part on a measurable change in at least one characteristic of surface plasmon-enhanced radiation (SPER) generated in proximity to the at least one chemical reaction.

In various aspects, the method further comprises irradiating a fluid or solid temperature-sensitive dielectric material with incident radiation, the dielectric material being contiguous with an electrically conductive film that includes at least one aperture formed therethrough so as to facilitate generation of the SPER based at least in part on the incident radiation, and disposing at least one reactant of the at least one chemical reaction in proximity to the dielectric material so as to be in thermal communication with the dielectric material, such that the enthalpy associated with the at least one chemical reaction causes a temperature change in the dielectric material, wherein the measurable change in the at least one characteristic of the SPER corresponds to the temperature change in the dielectric material.

Another embodiment is directed to an apparatus, comprising an electrically conductive film having a first surface, a second surface, and at least one aperture extending between the first surface and the second surface. The apparatus further comprises at least one temperature-sensitive fluid or solid dielectric material contiguous with at least a portion of the first surface of the electrically conductive film, and at least one reaction chamber disposed proximate to and in thermal communication with the dielectric material so as to facilitate a temperature change of the dielectric material due to at least one chemical reaction, when present, in the at least one reaction chamber.

Another embodiment is directed to an apparatus, comprising an electrically conductive film having a first surface, a second surface, and at least one aperture extending between the first surface and the second surface. The apparatus further comprises at least one temperature-sensitive fluid or solid dielectric material disposed on and contiguous with at least a portion of the first surface of the electrically conductive film. A temperature change of the dielectric material alters surface plasmon-enhanced radiation generated by the apparatus at the second surface via the at least one aperture, based on incident radiation, that when present, irradiates the first surface of the electrically conductive film, such that a measurable change in the surface plasmon-enhanced radiation represents the temperature change in the dielectric material.

Another embodiment is directed to a calorimetry system, comprising at least one temperature sensing apparatus. The at least one temperature sensing apparatus comprises an electrically conductive film having a first surface, a second surface, and at least one aperture extending between the first surface and the second surface. The temperature sensing apparatus also comprises a temperature-sensitive fluid or solid dielectric material disposed on and contiguous with at least a portion of the first surface of the electrically conductive film, and at least one reaction chamber disposed proximate to and in thermal communication with the dielectric material so as to facilitate a temperature change of the dielectric material due to an enthalpy associated with at least one chemical reaction, when present, in the at least one reaction chamber. The temperature change of the dielectric material alters surface plasmon-enhanced radiation (SPER) generated by the apparatus at the second surface via the at least one aperture, based on incident radiation, that when present, irradiates the first surface of the electrically conductive film, such that a measurable change in at least one characteristic of the SPER represents the temperature change in the dielectric material. The calorimetry system further comprises a radiation source to generate the incident radiation, at least one radiation detector to detect the SPER from the at least one temperature sensing apparatus, and a processor coupled to the at least one radiation detector to determine the enthalpy associated with the at least one chemical reaction based at least in part on the measurable change in the at least one characteristic of the SPER.

Another embodiment is directed to an apparatus, comprising a temperature-sensitive fluid or solid dielectric material, and at least one reaction chamber disposed proximate to the dielectric material and dimensioned so as to facilitate a hyperbolic heat transfer process between the at least one reaction chamber and the dielectric material due to at least one chemical reaction, when present, in the at least one reaction chamber. In various aspects of this embodiment, the at least one reaction chamber may includes an annular structure that surrounds the dielectric material, or at least one trough that is disposed adjacent to the dielectric material. In other aspects, the dielectric material may have a relaxation time on the order of nanoseconds, and the dielectric material and the at least one reaction chamber may be constructed and arranged such that a dimension over which the hyperbolic heat transfer process occurs is on the order of nanometers or tens of nanometers.

The term "radiation" should be understood to refer to any one or more of a variety of types of electromagnetic radiation including radiation within the visible spectrum, outside the visible spectrum, or a combination of both. Radiation may be generated by any suitable source, such as any one or more of a variety of active or passive radiation emitting devices configured to generate said radiation, including, but not limited to, various incoherent light sources (e.g., LED-based sources), various types of lasers, optical fibers, etc.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 4a and 4b illustrate respective top and cross-sectional side views of a temperature sensing apparatus according to another embodiment of the invention.

FIGS. 5a and 5b illustrate respective top and cross-sectional side views of a temperature sensing apparatus according to yet another embodiment of the invention.

FIGS. 11a and 11b are respective top and cross-sectional side views of a temperature sensor array according to another embodiment of the invention.

DETAILED DESCRIPTION

Figure 1:
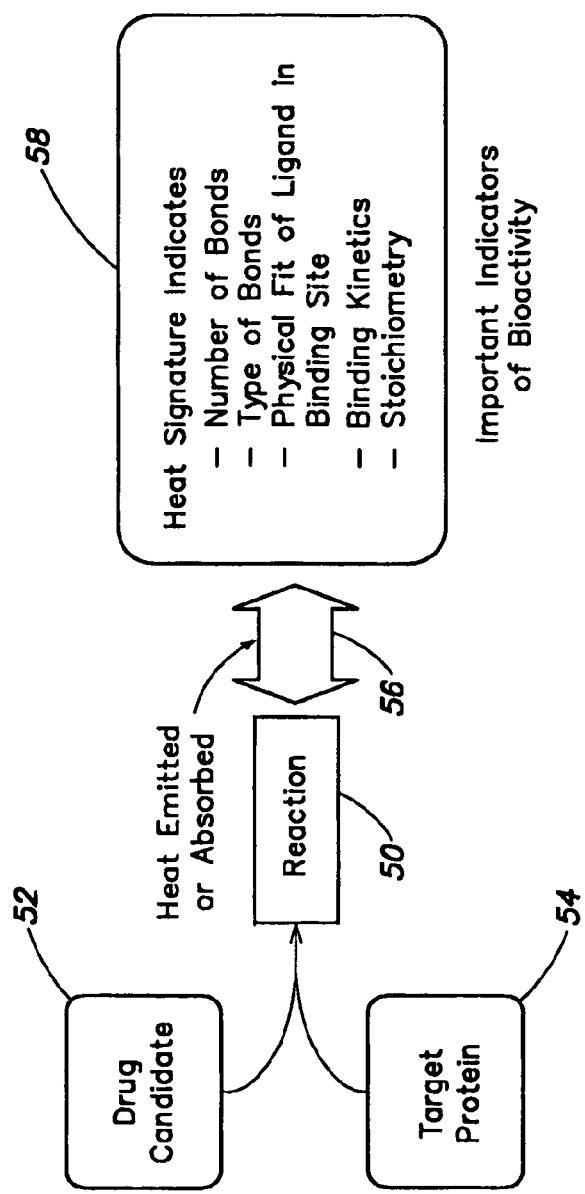
FIG. 1 is a schematic representation of a calorimetry process.

The present disclosure generally relates to inventive methods and apparatus for temperature sensing. In some embodiments disclosed herein, of interest are methods and apparatus for sensing temperature changes associated with a chemical reaction, so as to determine the thermodynamic characteristics of the reaction. Additionally, some embodiments, relate to methods and apparatus for facilitating a hyperbolic heat transfer process, as well as reducing heat losses by other means of heat transfer (such as by a Fourier heat transfer process).

Various aspects and embodiments of the present invention are described in further detail below, including certain embodiments relating particularly to temperature sensing associated with chemical reactions and calorimetry. It should be appreciated, however, that the present invention is not limited to any particular manner of implementation, and that the various embodiments discussed explicitly herein are provided primarily for purposes of illustration. The various concepts discussed herein may be suitably implemented for a variety of applications, including, but not limited to, nanoscale to microscale calorimetry for pharmaceutical and biotechnology products, combustion sensing, explosive detection, and biotoxin monitoring, as well as other applications that rely on measuring appreciably small temperature changes.

One illustrative embodiment of the invention relates to a temperature sensing apparatus based in part on an apparatus for generating surface plasmon-enhanced radiation (SPER), as disclosed in U.S. Pat. No. 7,318,907 to Stark et al., the entirety of which is incorporated by reference herein. To facilitate a discussion of this illustrative embodiment, some relevant aspects of Stark et al.'s SPER apparatus are discussed immediately below. However, it should be appreciated that various inventive methods and apparatus according to the present invention merely rely on some of the concepts disclosed in Stark et al. as a point of departure, and that these methods and apparatus significantly modify the functionality and structure of Stark et al. for the purposes of achieving ultra-sensitive temperature sensing.

In one disclosed example, Stark et al.'s SPER apparatus is employed as a biosensor to detect index of refraction changes as small as $10^{-5}\%$ caused by biochemical reactions occurring in proximity to a surface of the SPER apparatus. To achieve this sensitivity, the temperature of Stark et al.'s SPER-based biosensor must to be held constant to within ±0.001K. Accordingly, the teachings of Stark et al. essentially are antithetical to sensing temperature changes, as it is a mandatory requirement of Stark et al. to preclude temperature variations for proper operation of Stark et al.'s biosensor. Measurements made with the SPER-based biosensor disclosed in Stark et al. rely on detecting changes in the SPER generated by the apparatus when one of the reactants is immobilized on the surface of the SPER apparatus.

Figure 2A:
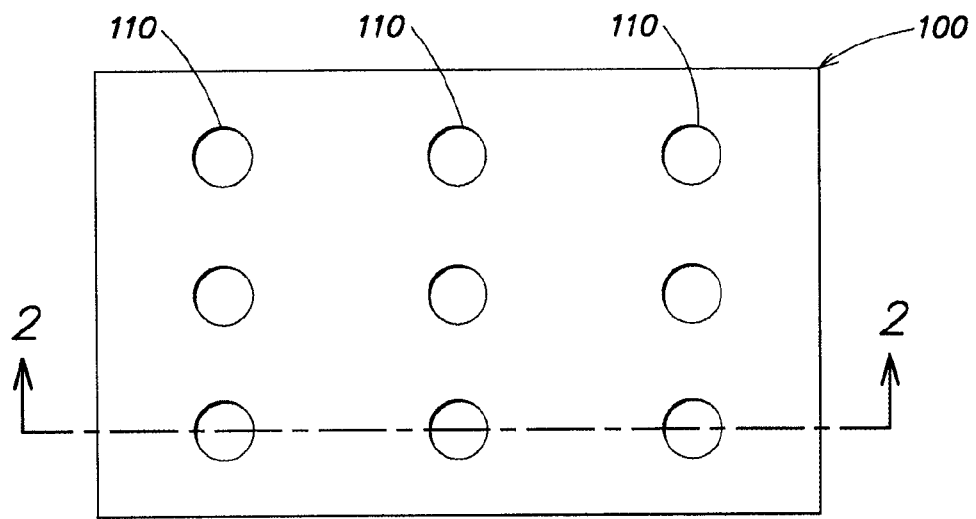
FIGS. 2a and 2b illustrate respective top and cross-sectional side views of a prior art nanohole array.
Figure 2B:
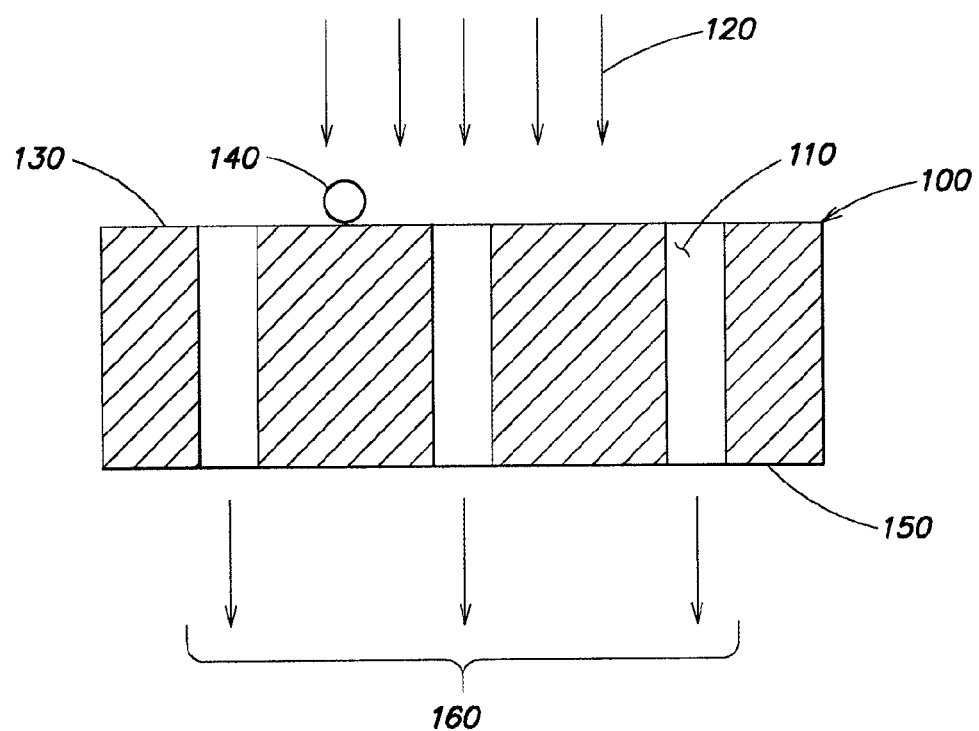

FIGS. 2a and 2b illustrate respective top and cross-sectional side views of Stark et al.'s SPER-based biosensor. An exemplary SPER apparatus comprises a 9×9 array of 150 nanometer apertures 110 on a 350 nanometer pitch in an electrically conductive (e.g., electrically conductive) film 100. Monochromatic collimated radiation 120 is incident upon a first surface 130 of the electrically conductive film 100, and the amount of SPER 160 generated by the apparatus is monitored. The array pitch is chosen to satisfy the grating momentum equation and the dispersion relation, allowing greatly-enhanced radiation transmission from the apparatus. In particular, the incident radiation 120 excites surface plasmons the first surface 130 of the electrically conductive film 100, and energy associated with the surface plasmons couples to an opposite surface 150 of the electrically conductive film 100, where the surface plasmon enhanced radiation (SPER) 160 is emitted from the apertures 110. A sample 140 immobilized on the first surface 130 of the electrically conductive film 100 corresponds to a binding reaction whose properties are to be measured by Stark et al.'s SPER-based biosensor. The generation of SPER is governed by the relative values of the dielectric constants of the sample and the electrically conductive film. In the biosensor of Stark et al., the temperature of the biosensor and sample are held constant so that any changes in the dielectric constant associated with the sample and affecting the SPER are due only to concentration changes representing reactions associated with the sample 140.

In contrast to the approach employed in Stark et al., Applicants have recognized and appreciated that an SPER apparatus may be employed to measure temperature changes associated with a chemical reaction rather than concentration changes. In particular, according to various embodiments of the present disclosure, an SPER apparatus may be particularly configured as an ultra-sensitive temperature sensing apparatus capable of measuring appreciably small temperature changes in an appreciably small volume in which a chemical reaction takes place. In some exemplary implementations discussed in greater detail below, a temperature change on the order of 0.0001K proximate to a surface of an SPER-based temperature sensing apparatus according to the present invention causes a corresponding change in radiation levels (e.g., intensity) generated by the apparatus by as much as 5%. As a result of the significant temperature sensitivity of such an apparatus, Applicants have recognized and appreciated that such apparatus may serve as an important basis for improved calorimetry techniques for a variety of applications.

Figure 3A:
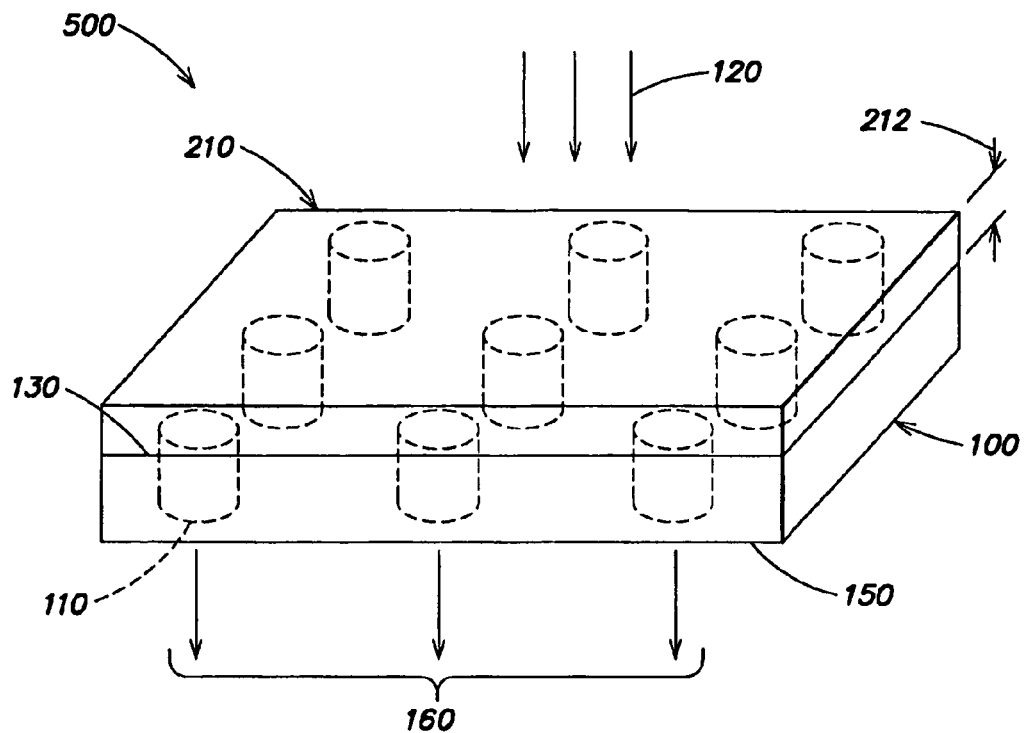
FIGS. 3a and 3b illustrate respective perspective and cross-sectional side views of a temperature sensing apparatus according to one embodiment of the present invention.
Figure 3B:
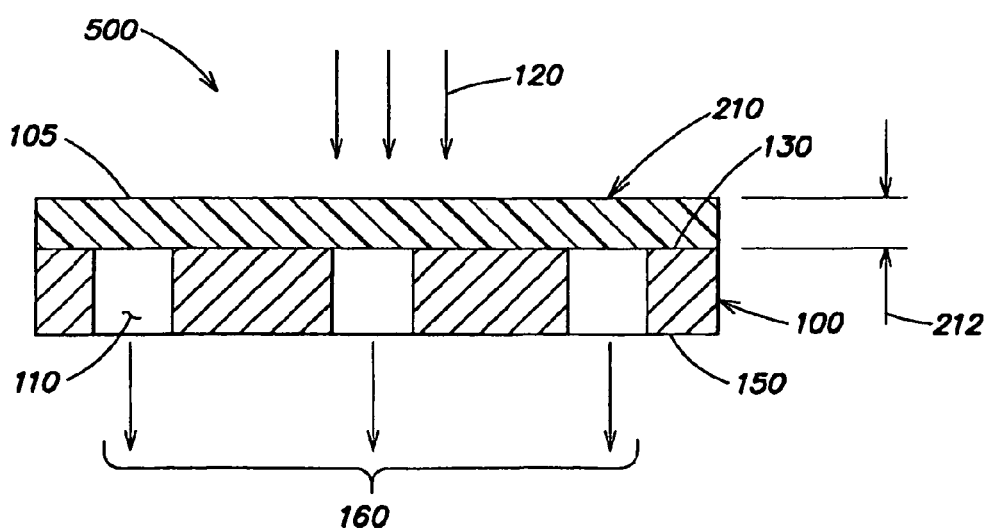

FIGS. 3a and 3b illustrate respective perspective and cross-sectional views of a temperature sensing apparatus 500 according to one embodiment of the present invention. In the embodiment of FIGS. 3a and 3b, a temperature-sensitive fluid and/or solid dielectric material 210 is disposed contiguous with a first surface 130 of an electrically conductive film 100 that includes one or more apertures 110 extending through the film. Incident radiation 120, when present, irradiates the dielectric material 210 and the first surface 130 of the electrically conductive film 100. A change in the temperature of the dielectric material 210 alters its dielectric constant, in turn changing plasmon excitation conditions in the electrically conductive film 100. This in turn affects an amount of SPER 160 that is emitted from the apertures 110 at a second surface 150 of the electrically conductive film 100.

In the embodiment of FIGS. 3a and 3b, the temperature change of the dielectric material 210 may result from a chemical reaction involving two or more reactants proximate to the dielectric material. In some exemplary implementations, energy released or absorbed by the reaction in the form of heat may cause a significant temperature change (e.g., greater than $10^{-3}$ K) in the dielectric material. Such a temperature change may form the basis for evaluative techniques such as calorimetry, in which the enthalpy of binding, equilibrium binding constant, and entropy changes associate with the chemical reaction are determined. In various embodiments discussed herein, temperature changes as small as 0.001K and as large as 50K may be measured via the apparatus 500, resulting in variations in SPER generated by the apparatus from approximately a few % to in excess of 10,000%. Of course, it should be appreciated that the foregoing values are provided primarily for the purposes of illustration, and that the present invention is not limited to these exemplary values.

In various other aspects, the dielectric material 210 of the apparatus 500 shown in FIGS. 3a and 3b may have a thickness 212 on the order of $\lambda/4$, where $\lambda$ is the wavelength of the incident radiation 120 (In exemplary implementation, incident radiation may have a wavelength of 635 nanometers corresponding to a HeNe laser). The dielectric material may be a liquid such as water, alcohol, glycerine, immersion oil, or a solid such as glass, quartz, saphile, or an optical polymer such as polycarbonate or polystyrene, or any other material having a dielectric function that is temperature dependent, at least over a particular temperature range of interest (e.g., based on the chemical reaction(s) to be monitored). One or more of the reactants may optionally be bound to a surface 105 of the dielectric material 210. Alternatively, in one implementation, the dielectric material 210 shown in FIGS. 3a and 3b may be a fluid serving as a solvent for one or more reactants of interest. In one aspect of such an embodiment, the fluid containing the reactants may be spotted on or flowed across the first surface 130 of the electrically conductive film 100 in any of a variety of known manners. In another aspect, the dielectric material 210 may be significantly transparent with respect to the incident radiation 120.

In the apparatus 500, the electrically conductive film 100 may be comprised of gold or other suitable electrically conductive materials, including, but not limited to, aluminum and/or silver. Although nine apertures 110 are shown in the electrically conductive film 100 so as to provide the structure for generating SPER, it should be appreciated that virtually any number of apertures may be used in various configurations, including a single aperture in the electrically conductive film, and that the invention is not limited to any particular number or arrangement of apertures 110 in the electrically conductive film 100. The SPER 160 may be detected by any suitable means, and similarly the invention is not limited in this respect. For example, any photodetector may be used including, but not limited to, photodiodes (including avalanche photodiodes), CCD cameras, CMOS devices, diode arrays, etc.

As with the biosensor of Stark et al., the apparatus 500 shown in FIGS. 3a and 3b is based at least in part on the excitation of surface plasmon on the first surface of the electrically conductive film, and altering the plasmon excitation conditions. These conditions are governed by the relationship (for normally incident radiation):

$$\lambda = \frac{a_0}{\gamma}\left(\frac{\varepsilon_1 \varepsilon_2}{\varepsilon_1 + \varepsilon_2}\right)^{\frac{1}{2}}$$

where $\varepsilon_1$ is the dielectric function of the dielectric material 210, $\varepsilon_2$ is the dielectric function of the first surface 130 of the electrically conductive film 100, the lattice constant $a_0$ is the center to center spacing of the apertures, $\gamma$ is an integer value, and $\lambda$ is the resonant wavelength of the apparatus (at which SPER is generated).

The equation above gives a resonance condition based on essentially monochromatic normally incident radiation 120, and is the result of combining the dispersion relation and the grating momentum equations and solving for the resonant wavelength. Unlike the biosensor of Stark et al., the embodiment of FIGS. 3a and 3b, as well as other embodiments contemplated by the present invention, exploit the relationship above by employing a temperature-sensitive fluid or dielectric material contiguous with at least a portion of the first surface of the electrically conductive film, such that $\varepsilon_1$ is a function of temperature. As $\varepsilon_1$ changes with temperature, the resonant wavelength $\lambda$ of the apparatus 500 changes. As the resonant wavelength $\lambda$ changes with respect to the spectrum/center wavelength of the incident radiation 120, the amount of SPER 160 ultimately generated by the apparatus varies. In this manner, by detecting changes in the transmission characteristics of the SPER 160, temperature changes in the dielectric material may be measured.

In other embodiments, a temperature sensing apparatus according to the present invention may additionally comprise one or more reaction chambers disposed proximate to the dielectric material 210, and positioned so as to facilitate a transfer of heat between the one or more reaction chambers and the dielectric material. In one exemplary implementation as shown in FIGS. 4a and 4b, the reaction chamber(s) may be disposed so as to be in the path of the incident radiation. In particular, FIGS. 4a and 4b show an embodiment of an apparatus 500, in which a reaction chamber 310, a dielectric material 210, an electrically conductive film 100 including one or more apertures 110, and a glass substrate 170 are disposed contiguously (e.g., consecutive with another) such that incident radiation 120, when present, passes through at least a portion of each. The reaction chamber 310 may contain one or more chemical substances that when brought together in any appropriate manner cause a chemical reaction that releases or absorbs heat. In one aspect of this embodiment, a solvent or medium for the reactants, any reagents, and/or reaction products should remain essentially transparent to the incident radiation, so that changes in the SPER 160 reflect only temperature changes due to the reaction. In other aspects, a system 1500 for conducting studies (e.g., calorimetry) based on the temperature sensing apparatus 500 may include a radiation source 180 (e.g., HeNe laser) to provide the incident radiation 120, a radiation detector 190 (e.g., CCD camera, photomultipliers, etc.) to detect the SPER 160, and at least one processor 550 coupled to the radiation detector to determine the enthalpy associated with the reaction based at least in part on a change in the SPER 160.

Figure 6:
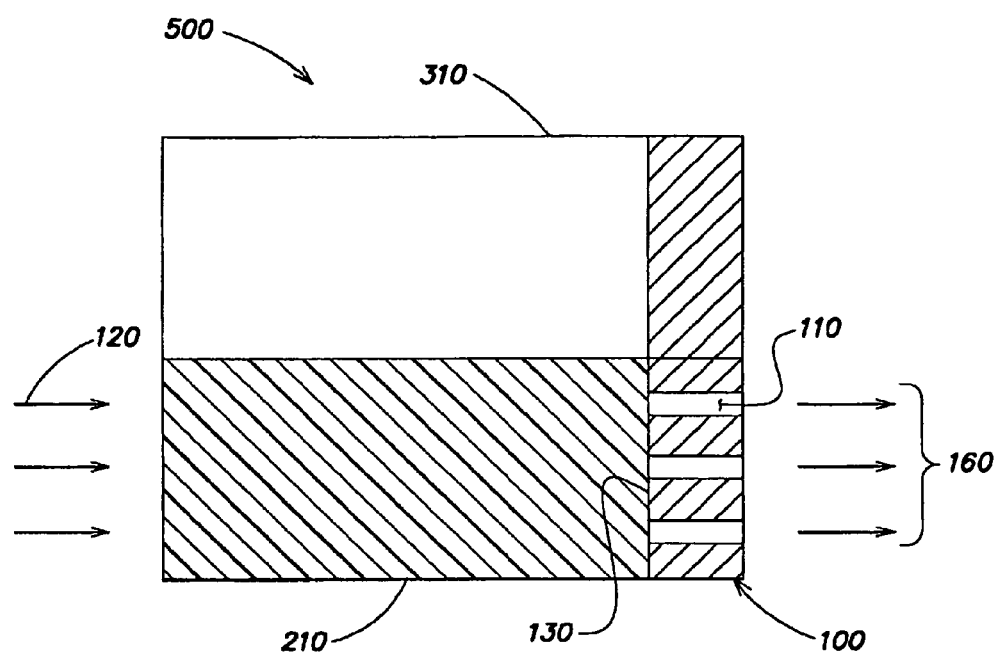
FIG. 6 illustrates a cross-sectional side view of a temperature sensing apparatus according to yet another embodiment of the invention.

In some alternative embodiments, as shown for example in FIGS. 5a, 5b, and 6, one or more reaction chambers 310 are disposed such that they are not in the path of the incident radiation 120. For example, in the embodiment shown in FIGS. 5a and 5b, the reaction chamber 310 is formed as a circular annular well structure that surrounds the dielectric material 210. In one exemplary implementation of the apparatus shown in the embodiment of FIGS. 5a and 5b, a 100 nanometer thick electrically conductive film 100 is deposited on a transparent glass substrate 170 using any suitable means, and apertures 110 with an approximate diameter of 150 nanometers (and an approximate pitch of 350 nanometers for multiple apertures) are created into the electrically conductive film using known microfabrication techniques, including, but not limited to, ion beam milling and lithography. A thin (e.g., 75-150 nanometers) dielectric material (e.g., polycarbonate) is then deposited on the electrically conductive film 100. The reaction chambers 310 may be formed by etching the dielectric material 210 using photolithography, wet or dry etching, or any other suitable technique.

In yet other embodiments, one or more reaction chambers may form one or more troughs that run adjacent to the dielectric material (e.g., so as to facilitate an integration of microfluidics with the temperature sensing apparatus). In some embodiments, a depth 215 of a well or trough serving as a reaction chamber 310 may be equal to, less than, or larger than a depth of the dielectric material. In one embodiment shown in FIG. 6, a reaction chamber 310 is disposed on only one side of the dielectric material 210, the dielectric material 210 and the electrically conductive film 100 both being within the path of the incident radiation 120. In one exemplary implementation, the reaction chamber 310 depicted in FIG. 6 may be a combustion chamber.

Irrespective of the location of the reaction chamber(s) with respect to the incident radiation, the heat generated or absorbed in a reaction chamber changes the temperature of the dielectric material (dielectric function $\in_1$), and as such allows for the creation of a simpler system than if the reactants were in direct thermal contact with the first surface of the electrically conductive film (dielectric function $\in_2$). As discussed above in connection with FIG. 4, if the reactants or solvent for the reactants were serving as the dielectric (dielectric function $\in_1$) then the photonic coupling conditions would potentially differ for every reactant pair, requiring assay development work, and as the reactants bind their changing concentrations could result in changes in $\in_1$.

Figure 7:
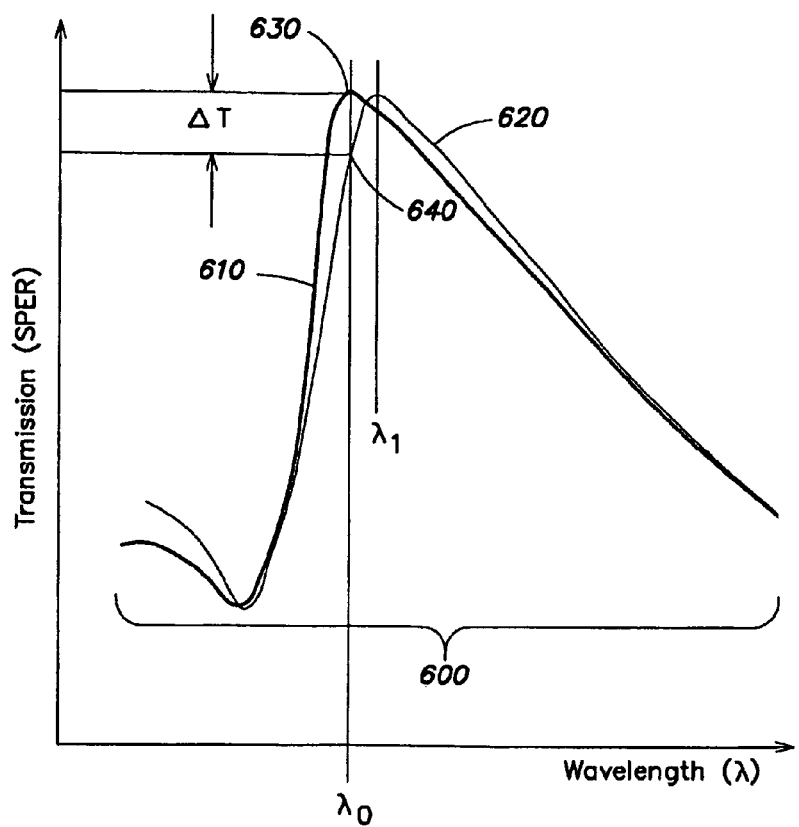
FIG. 7 is a diagram depicting changes in generated surface-plasmon radiation as a function of temperature at a particular wavelength, according to various embodiments of the invention.

In a temperature sensing apparatus 500 according to various embodiments of the present invention, determination of temperature changes in the dielectric material 210 contiguous with the first surface of the electrically conductive film is based on measurements of SPER from the second surface of the electrically conductive film. As discussed above, and illustrated in FIG. 7, the amount of SPER is temperature dependent due to the temperature-sensitive dielectric function of the dielectric material adjacent to the electrically conductive film, which changes the plasmon excitation conditions with temperature variations. For example, as shown in FIG. 7, a change in the temperature ($\Delta T$) of the dielectric material 210 causes a corresponding shift in the SPER spectrum 600 from position 610 to position 620 (i.e., the resonant wavelength of the apparatus shifts between $\lambda_0$ to $\lambda_1$ for a change in temp $\Delta T$). Accordingly, the level of generated SPER based on incident radiation at a selected wavelength ($\lambda_0$) changes from a first value 630 to a second value 640. SPER versus time is then recorded at the selected incident wavelength ($\lambda_0$), and a temperature change ($\Delta T$) associated with the change in SPER as a function of time may accordingly be determined.

Figure 8:
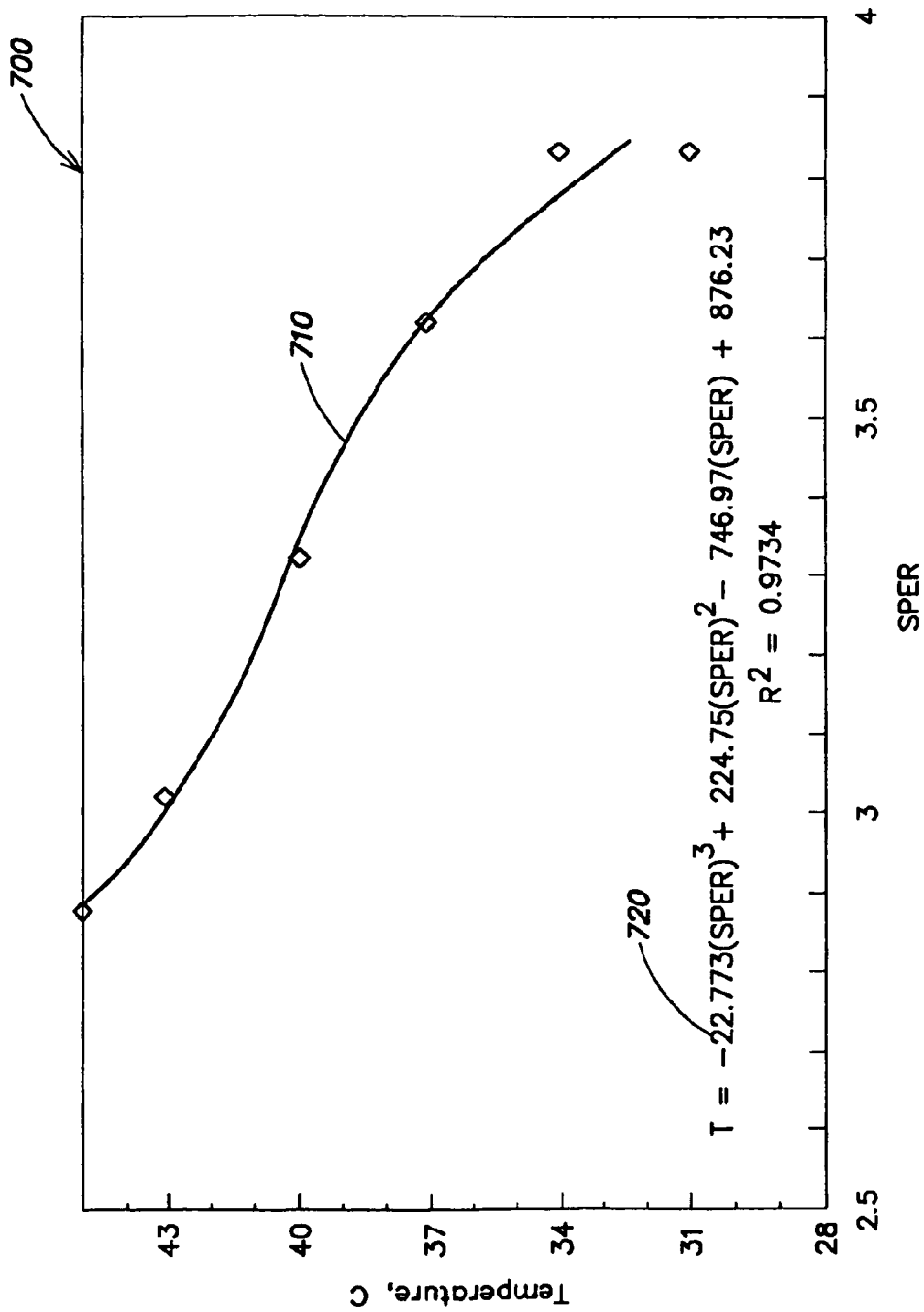
FIG. 8 is a calibration curve relating temperature to generated surface-plasmon radiation, according to another embodiment of the invention.

In another aspect of various embodiments disclosed herein, the temperature sensitivity of a given temperature sensing apparatus 500 over some range of temperatures of interest can be measured and displayed as a calibration plot 700, as shown in FIG. 8. For example, a calibration curve 710 may be calculated by increasing the temperature of a dielectric material in precise known steps over a desired temperature range using any known method, and measuring the SPER signal after the thermal conditions of the dielectric material have reached a steady state for each temperature step. From the measured SPER quantities, a relationship 720 between temperature and SPER for the temperature sensing apparatus is determined by fitting a best-fit curve to the data. $R^2$ is a measure of the quality of the fit of the relationship 720 to measured SPER. The calibration plot 700 shown in FIG. 8 illustrates the relationship between temperature (y-axis of FIG. 8) and SPER (x-axis of FIG. 8). However, as should be readily appreciated by one skilled in the art, a corresponding relationship between $\Delta T$ and SPER would be simply derived from the calibration curve 710 given the availability of temperature versus time data. The exemplary temperature-SPER relationship 720 shown in FIG. 8 is of third order; however, it should be appreciated that a polynomial expression of any order may be used to represent a relationship between temperature and SPER generation (e.g., irradiance).

Measurable changes in SPER characteristics (e.g., irradiance), as a consequence of changes in $\in_1$ of the dielectric material, provides a basis for a calorimetry method according to one embodiment of the present invention, in which the enthalpy of a chemical reaction is determined. In particular, a change in the average temperature of the dielectric material proximate to the chemical reaction (e.g., proximate to a reaction chamber in which the reaction occurs) is related to the amount of heat released or absorbed by (i.e., the enthalpy) the reaction. More specifically, an energy balance (i.e., conservation of energy) on the dielectric material and the reaction chamber allows the molar heat of interaction (i.e., enthalpy: $(n_{AB}\Delta H)_F$) of a chemical reaction occurring in the chamber to be determined from the observed temperature rise in the dielectric material according to $$(n_{AB}\Delta H)_F = (n_{AB}\Delta H)_I + \left[\frac{(\rho cV)_{rc}F_{\Delta T} + (\rho cV)_d}{(1 - F_{\Delta H})}\right](T_d - T_I)$$

where $n_{AB}$ is the molar product ratio of the reactants A and B, $(n_{AB}\Delta H)_I$ is the energy released by the reaction during an Ith titration, $(\rho cV)_{rc}$ is the density-specific heat-volume product of the reaction chamber, $(\rho cV)_d$ is the density specific heat-volume product of the dielectric material, $F_{\Delta T}$ and $F_{\Delta H}$ are calibration parameters relating the temperatures in the reaction chamber and the molar heat of interaction to the heat loss, respectively, $T_d$ equals the measured temperature of the dielectric material and $T_I$ is the initial temperature of the dielectric material at the start of the Ith titration. The calibration factors, $F_{\Delta T}$ and $F_{\Delta H}$, may be measured during the initial verification testing of the device. It is assumed that the initial temperature $T_I$ and the initial value of the enthalpy $(n_{AB}\Delta H)_I$ are known at the start of any titration; for example, $n_{AB}$ is zero and $(n_{AB}\Delta H)_I$ is zero for the first titration.

Figure 9A:
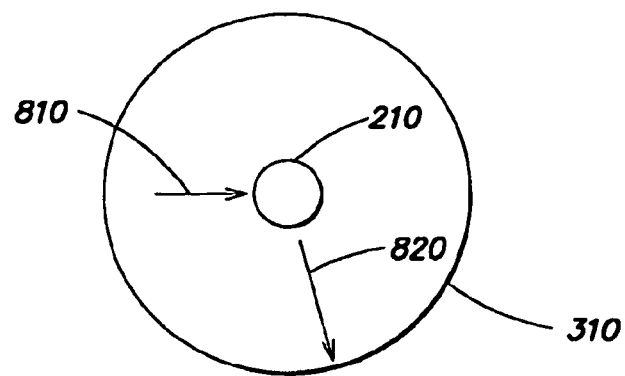
FIGS. 9a and 9b are respective top and cross-sectional side views of a heat-transfer apparatus according to another embodiment of the invention.
Figure 9B:
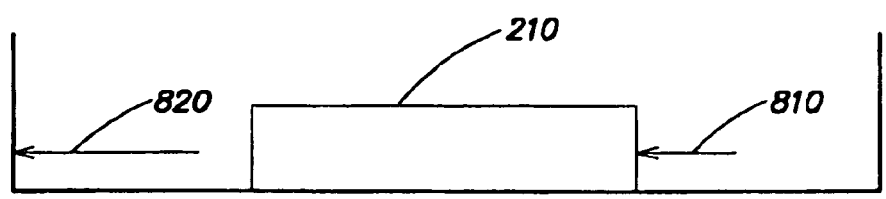

As illustrated with the aid of FIGS. 9a and 9b, heat transfer from the reaction chamber to the dielectric material may occur through at least two thermal transport models, namely Fourier and hyperbolic heat transfer. Significantly different transient (temporal) and spatial temperature fields exist between the hyperbolic and Fourier heat transfer regimes for biological materials. The response of a material to a change in temperature is governed in part by the material's relaxation time. Materials with short relaxation times on the order of a few nanoseconds are more likely to support heat transfer in the hyperbolic regime. Exemplary dielectric materials for use in various embodiments of the temperature sensing apparatus, such as polycarbonate, have relaxation times on the order of a few nanoseconds, and a typical time constant for a reaction of a few molecules is also on the order of a few nanoseconds. Thus, the temperature-related characteristics of both exemplary dielectric materials and reactions contemplated by various embodiments of the present invention facilitate heat transfer in the hyperbolic regime.

An appropriate heat transfer model may also be determined based in part on the distance scale (spatial extent) over which the thermal energy travels. At small distance scales (on the order of tens of nanometers), hyperbolic heat transfer mechanisms (see FIG. 9, arrow 810) dominate, and thermal pulses are assumed to travel at finite speeds. By contrast, at large distance scales, Fourier heat transfer mechanisms (see FIG. 9, arrow 820) dominate, and thermal pulses are assumed to travel infinitely fast.

In view of the foregoing, Applicants have recognized and appreciated that methods and apparatus that facilitate hyperbolic heat transfer between one or more reaction chambers and a dielectric material may improve the sensitivity of a temperature sensing apparatus by improving the heat transfer coupling between the reaction chamber and the dielectric material. As such, some embodiments of the invention are directed to methods and apparatus for facilitating hyperbolic heat transfer. For example, exemplary implementations of the reaction chamber(s) 310 include chamber dimensions on the order of 50-100 nanometers, and are therefore designed to facilitate heat transfer in the hyperbolic regime. Furthermore, the choice of dielectric materials as stated above, also serves to facilitate hyperbolic heat transfer (e.g., based on material relaxation times).

Figure 10:
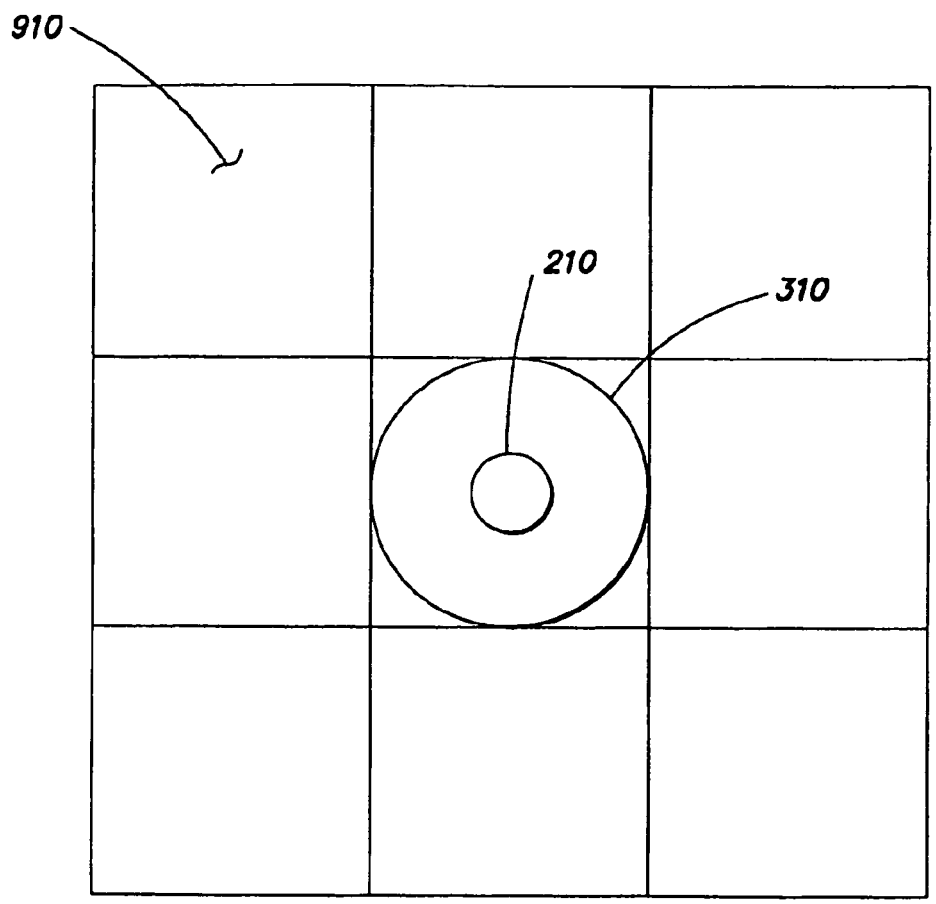
FIG. 10 is a top-view of a thermally-buffered temperature sensor according to another embodiment of the invention.

Applicants also have recognized and appreciated that a potential source of reduced sensitivity for a temperature sensing apparatus according to various embodiments of the present invention includes heat transfer from a reaction chamber via surfaces other than the surface in contact with the dielectric material. In an ideal case, all of the heat transfer from the reaction chamber would be directed to the dielectric material, and the rest of the system would be adiabatic. As such, another embodiment of the present invention employs thermal buffering to reduce heat transfer through boundaries of a reaction chamber that are not in contact with the dielectric material (e.g., the exterior sides of a reaction chamber as shown in FIG. 10). In one embodiment shown in FIG. 10, additional secondary chambers 910 surround a primary reaction chamber 310 and provide thermal buffering to the primary chamber 310. In one aspect of this embodiment, the secondary chambers 910 contain the same reactants as the primary chamber 310 and shield the heat transfer from the sides of the primary chamber 310, providing for an increased sensitivity of the primary sensor.

Applicants have also recognized that heat transfer through a lower surface of a reactant chamber may also reduce the sensitivity of a temperature sensing apparatus, particularly if the lower surface of the reactant chamber is in contact with a highly conductive surface, such as the electrically conductive film 100. To reduce heat transfer through the bottom of the reactant chamber(s), some embodiments may additionally comprise an insulating layer (see 415 in FIG. 5) with a thermal conductivity less than the thermal conductivity of the electrically conductive film 100, the insulating layer 415 disposed between the bottom of the one or more reactant chambers 310 and the electrically conductive film 100 containing the aperture(s) 110.

Applicants have also recognized that heat transfer through the upper surface of a reactant chamber may also decrease the sensitivity of the apparatus. As such, in some embodiments, a temperature sensing apparatus 500 may be housed in an isolation chamber that maintains a stable temperature within the isolation chamber, and optionally includes a humidity control chamber for reducing heat loss by evaporation from a reaction chamber. It should be appreciated, of course, that the stable environmental temperature maintained by such an isolation chamber would not preclude temperature changes resulting from the reaction of interest and causing changes in the dielectric function $\in_1$ of the dielectric material.

In yet other embodiments, multiple temperature sensing apparatuses according to the invention may be organized into a temperature sensor array that may, for example, facilitate a high-throughput screening of biological and/or chemical substances. An example of such a temperature sensor array 1000 is shown in FIGS. 11a and 11b. In one exemplary implementation, respective temperature sensing apparatus 500 are arranged in a plane corresponding to the electrically conductive film 100. While the apparatus 500 shown in FIGS. 11a and 11b correspond generally to the structure shown in FIG. 5, it should be readily appreciated by those skilled in the art that any temperature sensing apparatus pursuant to the concepts disclosed herein may be fabricated into an array 1000 such as that depicted in FIGS. 11a and 11b to facilitate multiple temperature sensing measurements. For example, a temperature sensor array 1000 according to various embodiments of the invention may comprise apparatus 500 with or without reaction chambers 310, and/or apparatus 500 with reaction chambers 310 in or out of the path of incident radiation 120. Also, it should be appreciated that while a two-dimensional array of eight temperature sensing apparatus 500 is shown in FIG. 11a, temperature sensor arrays according to the present invention are not limited in this respect, as virtually any number of apparatus 500 may be employed in an array 1000 and arranged in any of a variety of configurations (e.g., one-dimensional linear or curvilinear arrays, two-dimensional configurations having various geometries, etc.)

In one exemplary implementation, each of the apparatus 500 in the temperature sensing array 1000 shown in FIG. 11b comprises an electrically conductive film having a first surface 130, a second surface 150, at least one aperture 110 extending between the first surface 130 and the second surface 150, and at least one temperature-sensitive fluid and/or solid dielectric material 210 contiguous with at least a portion of the first surface 130 of the electrically conductive film 100. In some implementations, disposed proximate to the dielectric material 210 of each apparatus 500 is at least one reaction chamber 310 placed so as to facilitate a change in the temperature of the dielectric material 210 due to at least one chemical reaction, when present, in the at least one reaction chamber 310. In one aspect of various embodiments directed to temperature sensor arrays, the respective temperature sensing apparatus 500 may or may not be identical. For example, at least some of the apparatus 500 may contain different dielectric materials, and/or have reaction chambers that contain different chemical reactions.

In another aspect of various embodiments directed to temperature sensor arrays, the respective temperature sensing apparatus 500 may have different aperture sizes, geometries and/or arrangements in the electrically conductive (metal) film. For example, the electrically conductive film 100 and aperture(s) 110 of respective apparatus 500 may be designed and/or arranged such that at least some of the apparatus 500 are configured to provide different plasmon excitation and/or resonance conditions than other apparatus of the array. As discussed in detail in U.S. Pat. No. 7,318,907 to Stark et al., incorporated by reference herein, the size, pitch, and/or particular geometric arrangement of apertures in the electrically conductive film affects the plasmon excitation/resonance conditions for generating SPER. The ability to tailor the resonance frequency of different apparatus in the array, alone or in combination with a number of possible different dielectric materials and reaction chamber arrangements that may be employed in a given temperature sensor apparatus pursuant to the concepts disclosed herein, provides for a rich variety of possible implementations for temperature sensor arrays according to the present disclosure.

Temperature sensor arrays such as shown in FIG. 11a and 11b enable the simultaneous measurement of confounding effects (e.g., buffer dilution, mixing, contaminants in the buffer solution, heat transfer effects), and allow for deconvolution of these effects to more accurately determine the enthalpy associated with a reaction. As such, some of the apparatus 500 in the temperature sensor array 1000 may be used as control sensors, which may be used to detect confounding thermodynamic effects such as dilution, protein conformation changes, and temporal variations in the irradiance of the radiation source. For example, some of the apparatus 500 may be used as calibration sensors to detect an irradiance signal from the radiation source, and use the irradiation signal to calibrate the "active" sensors which comprise reaction chambers where one or more chemical reactions may occur. Additionally, the signal from each apparatus 500 in the temperature sensor array 1000 may be normalized using an initial baseline, so small spatial and temporal variations in irradiance are reduced. One or more apparatus 500 in a temperature sensor array 1000 may also be used to provide redundant measurements, if desired. Alternatively, multiple apparatus 500 in a temperature sensor array may be used to measure temperature changes for different chemical reactions in the same experiment, allowing for the array 1000 to be used as a calorimetric-based high throughput screening method.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A calorimetry method, comprising:
A) determining an enthalpy associated with at least one chemical reaction based at least in part on a measurable change in at least one characteristic of surface plasmon-enhanced radiation (SPER) generated in proximity to the at least one chemical reaction.

2. The method of claim 1, wherein A) comprises:
B) irradiating a fluid or solid temperature-sensitive dielectric material with incident radiation, the dielectric material being contiguous with an electrically conductive film that includes at least one aperture formed therethrough so as to facilitate generation of the SPER based at least in part on the incident radiation; and
C) disposing at least one reactant of the at least one chemical reaction in proximity to the dielectric material so as to be in thermal communication with the dielectric material, such that the enthalpy associated with the at least one chemical reaction causes a temperature change in the dielectric material,
wherein the measurable change in the at least one characteristic of the SPER corresponds to the temperature change in the dielectric material.

3. The method of claim 2, wherein A) further comprises:
D) determining the temperature change of the dielectric material based on the measurable change in the at least one characteristic of the SPER; and
E) determining the enthalpy associated with the at least one chemical reaction based at least in part on D) and a density-specific heat-volume product of the dielectric material.

4. The method of claim 3, wherein C) comprises:
disposing the at least one reactant of the at least one chemical reaction in proximity to the dielectric material so as to facilitate a hyperbolic heat transfer process between the at least one chemical reaction and the dielectric material.

5. The method of claim 2, wherein the dielectric material is a fluid containing the at least one reactant, and wherein the method further comprises:
disposing the fluid on the electrically conductive film.

6. The method of claim 3, wherein C) comprises:
disposing the at least one reactant in at least one reaction chamber proximate to the dielectric material.

7. The method of claim 6, wherein the at least one reaction chamber is arranged with respect to the dielectric material such that the at least one reaction chamber is not in a path of the incident radiation.

8. The method of claim 6, wherein E) further comprises:
F) determining the enthalpy associated with the at least one chemical reaction based on an energy balance between the at least one reaction chamber and the dielectric material.

9. The method of claim 8, wherein F) comprises:
G) determining the enthalpy associated with the at least one chemical reaction based at least in part on the temperature change of the dielectric material, the density-specific heat-volume product of the dielectric material, and a density-specific heat-volume product of the reaction chamber.

10. The method of claim 8, wherein F) comprises:
determining the enthalpy associated with the at least one chemical reaction based at least in part on at least one calibration parameter relating to a heat loss in the at least one reaction chamber.

11. An apparatus, comprising:
an electrically conductive film having a first surface, a second surface, and at least one aperture extending between the first surface and the second surface;
at least one temperature-sensitive fluid or solid dielectric material contiguous with at least a portion of the first surface of the electrically conductive film; and
at least one reaction chamber disposed proximate to and in thermal communication with the dielectric material so as to facilitate a temperature change of the dielectric material due to at least one chemical reaction, when present, in the at least one reaction chamber.

12. The apparatus of claim 11, wherein the at least one reaction chamber is disposed with respect to the dielectric material so as not to obstruct the at least one aperture from incident radiation that, when present, irradiates the first surface of the electrically conductive film.

13. The apparatus of claim 11, wherein the at least one reaction chamber includes an annular well that surrounds the dielectric material.

14. The apparatus of claim 11, wherein the at least one reaction chamber includes at least one trough disposed adjacent to the dielectric material.

15. The apparatus of claim 13, wherein:
the dielectric material is formed as an essentially planar film extending across at least the portion of the first surface of the electrically conductive film, the dielectric material having a thickness along a direction normal to the first surface of the metal film; and
the at least one reaction chamber is formed as an etched portion of the dielectric material, the at least one reaction chamber having a depth along the direction normal to the first surface of the electrically conductive film.

16. The apparatus of claim 15, wherein the depth of the at least one reaction chamber is equal to or less than the thickness of the dielectric material.

17. The apparatus of claim 15, wherein the depth of the at least one reaction chamber is greater than the thickness of the dielectric material.

18. The apparatus of claim 15, further comprising at least one thermally insulating material disposed between the at least one reaction chamber and the electrically conductive film.

19. The apparatus of claim 11, wherein the at least one reaction chamber is disposed with respect to the dielectric material so as to facilitate a hyperbolic heat transfer process between the at least one reaction chamber and the dielectric material.

20. The apparatus claim 11, wherein the temperature change of the dielectric material alters surface plasmon-enhanced radiation (SPER) generated by the apparatus at the second surface of the electrically conductive film via the at least one aperture, based on incident radiation that, when present, irradiates the first surface of the electrically conductive film, such that a measurable change in the surface plasmon-enhanced radiation represents the temperature change in the dielectric material.

21. The apparatus of claim 11, wherein the dielectric material includes polycarbonate.

22. A temperature sensor array comprising a plurality of apparatus according to claim 11.

23. The temperature sensor array of claim 22, wherein a first apparatus of the array includes a first dielectric material, wherein a second apparatus of the array includes a second dielectric material, and wherein the first dielectric material and the second dielectric material are different.

24. The temperature sensor array of claim 22, wherein a first reaction chamber associated with a first apparatus of the array includes a first chemical reaction, wherein a second reaction chamber associated with a second apparatus of the array includes a second chemical reaction, and wherein the first chemical reaction and the second chemical reaction are different.

25. The temperature sensor array of claim 22, wherein a first apparatus of the array includes a first configuration of a first at least one aperture in a first electrically conductive film to provide a first resonance condition for the first apparatus, wherein a second apparatus of the array includes a second configuration of a second at least one aperture in a second electrically conductive film to provide a second resonance condition for the second apparatus, and wherein the first resonance condition and the second resonance condition are different.

26. The temperature sensor array of claim 22, wherein the plurality of apparatus are arranged such that at least one apparatus of the plurality of apparatus is configured to reduce a heat loss from at least one other apparatus of the plurality of apparatus.

27. The temperature sensor array of claim 26, wherein the at least one apparatus includes a first group of the plurality of apparatus arranged as a plurality of thermal buffers to reduce the heat loss from the at least one other apparatus.

28. The temperature sensor array of claim 27, wherein the first group of the plurality of apparatus are arranged so as to surround the at least one other apparatus.

29. An apparatus, comprising:
an electrically conductive film having a first surface, a second surface, and at least one aperture extending between the first surface and the second surface; and
at least one temperature-sensitive fluid or solid dielectric material disposed on and contiguous with at least a portion of the first surface of the electrically conductive film,
wherein a temperature change of the dielectric material alters surface plasmon-enhanced radiation generated by the apparatus at the second surface via the at least one aperture, based on incident radiation that, when present, irradiates the first surface of the electrically conductive film, such that a measurable change in the surface plasmon-enhanced radiation represents the temperature change of the dielectric material.

30. A calorimetry system, comprising:
at least one temperature sensing apparatus, comprising:
an electrically conductive film having a first surface, a second surface, and at least one aperture extending between the first surface and the second surface;
a temperature-sensitive fluid or solid dielectric material disposed on and contiguous with at least a portion of the first surface of the electrically conductive film;
at least one reaction chamber disposed proximate to and in thermal communication with the dielectric material so as to facilitate a temperature change of the dielectric material due to an enthalpy associated with at least one chemical reaction, when present, in the at least one reaction chamber,
wherein the temperature change of the dielectric material alters surface plasmon-enhanced radiation (SPER) generated by the apparatus at the second surface via the at least one aperture, based on incident radiation that, when present, irradiates the first surface of the electrically conductive film, such that a measurable change in at least one characteristic of the SPER represents the temperature change of the dielectric material,
the calorimetry system further comprising:
a radiation source to generate the incident radiation;
at least one radiation detector to detect the SPER from the at least one temperature sensing apparatus; and
a processor coupled to the at least one radiation detector to determine the enthalpy associated with the at least one chemical reaction based at least in part on the measurable change in the at least one characteristic of the SPER.

* * * * *